US007142664B2

(12) United States Patent
Seligmann

(10) Patent No.: US 7,142,664 B2
(45) Date of Patent: Nov. 28, 2006

(54) INTELLIGENT MULTIMODE MESSAGE ALERTS

(75) Inventor: Doree Duncan Seligmann, New York, NY (US)

(73) Assignee: Avaya Technology Corp., Basking Ridge, NJ (US)

(*) Notice: Subject to any disclaimer, the term of this patent is extended or adjusted under 35 U.S.C. 154(b) by 419 days.

(21) Appl. No.: 10/263,616

(22) Filed: Oct. 3, 2002

(65) Prior Publication Data

US 2004/0066932 A1 Apr. 8, 2004

Related U.S. Application Data

(60) Provisional application No. 60/380,140, filed on May 6, 2002.

(51) Int. Cl.
*H04M 1/00* (2006.01)
(52) U.S. Cl. ............................ 379/373.01; 379/373.02; 379/372
(58) Field of Classification Search ................ 379/372, 379/373.01, 373.02
See application file for complete search history.

(56) References Cited

U.S. PATENT DOCUMENTS

| 5,481,590 | A | 1/1996 | Grimes |
| 5,790,974 | A | 8/1998 | Tognazzini |
| 5,938,721 | A | 8/1999 | Dussell et al. |
| 6,026,156 | A | 2/2000 | Epler et al. |
| 6,222,482 | B1 | 4/2001 | Gueziec |
| 6,356,533 | B1 | 3/2002 | Bruno et al. |
| 6,411,687 | B1 | 6/2002 | Bohacek et al. |
| 6,434,404 | B1 | 8/2002 | Claxton et al. |
| 6,535,748 | B1 | 3/2003 | Vuorio et al. |
| 6,542,584 | B1 | 4/2003 | Sherwood et al. |
| 6,763,105 | B1 * | 7/2004 | Miura et al. ............ 379/373.01 |
| 6,917,680 | B1 * | 7/2005 | Korn et al. ............. 379/373.01 |
| 7,024,229 | B1 * | 4/2006 | Nishimura ............. 379/373.02 |
| 2002/0010008 | A1 * | 1/2002 | Bork et al. ................. 455/567 |
| 2002/0059434 | A1 | 5/2002 | Karaoguz et al. |
| 2002/0086680 | A1 | 7/2002 | Hunzinger |
| 2002/0089421 | A1 | 7/2002 | Farringdon et al. |
| 2002/0094076 | A1 * | 7/2002 | Chen ...................... 379/373.01 |
| 2003/0039339 | A1 | 2/2003 | Luehrig et al. |
| 2003/0054865 | A1 | 3/2003 | Byers et al. |
| 2004/0067751 | A1 * | 4/2004 | Vandermeijden et al. 379/88.19 |

FOREIGN PATENT DOCUMENTS

| EP | 1008946 | | 6/2000 |
| EP | 1172991 A1 * | | 1/2002 |
| GB | 2303271 A | | 2/1997 |
| JP | 09113599 | | 2/1997 |
| WO | WO 97/50231 | | 12/1997 |

* cited by examiner

*Primary Examiner*—Jefferey F. Harold
(74) *Attorney, Agent, or Firm*—DeMont & Breyer LLC

(57) ABSTRACT

An apparatus that intelligently determines how to alert a user to the arrival of an incoming message at a telecommunications terminal, and what information is imparted to the user via the alert, is disclosed. In the illustrative embodiments, the terminal has a processor that makes this determination based on one or more of the following: properties of the incoming message (e.g., who sent the message, a priority level associated with the message, the semantic content of the message, the length of the message, etc.), the time and date (i.e., the "calendrical time"), environmental parameters (e.g., temperature, ambient luminosity, etc.), the user's physiological parameters (e.g., blood pressure, heart rate, etc.), the location of the user, the proximity of other wireless terminals in the vicinity, whether the user is currently receiving another message, and the delivery mechanism of the other message (e.g., voice, text chat, etc.).

20 Claims, 8 Drawing Sheets

INTELLIGENT MULTIMODE MESSAGE ALERTS

STATEMENT OF RELATED APPLICATIONS

This application claims the benefit of U.S. Provisional Patent Application 60/380,140, filed on 6 May 2002, entitled "Method for Interception, Manipulations, and Usage of Bluetooth Voice Streams."

FIELD OF THE INVENTION

The present invention relates to telecommunications equipment in general, and, in particular, to a telecommunications terminal that intelligently decides how to alert the user to the arrival of an incoming message.

BACKGROUND OF THE INVENTION

FIG. 1 depicts a rendering of an exemplary subnetwork attached to public switched telephone network (PSTN) 100. The subnetwork comprises: PBX 120, cellular network 150, and five telecommunications terminals: wireline telephones 110-1 and 110-2, cordless telephone 130, wireless telephone 160, and two-way pager 170. As shown in FIG. 1, PBX 120's antenna 125 communicates wirelessly with wireless telephone 130's antenna 135, and cellular network 150's antenna 155 communicates wirelessly with wireless telephone 160's antenna 165 and two-way pager 170's antenna 175. Telecommunications terminals, such as those depicted in FIG. 1, alert a user when the terminal receives an incoming message.

In the prior art, a telecommunications terminal typically alerts the user to the arrival of an incoming message via some sensory mechanism; most commonly, this mechanism is an acoustic "telephone ring". In some telecommunications terminals, it is possible for the user to specify one of a plurality of such sensory mechanisms; for example, some wireless telephones give the user a choice of an acoustic "telephone ring" or a physical vibration of the telecommunications terminal. However, the sensory mechanism selected by the user applies to all incoming messages.

In the prior art, some telecommunications terminals alert the user to the arrival of an incoming message via more than one sensory mechanism; for example, a telecommunications terminal with "caller ID" service can provide a visual text message indicating the identity of the caller in addition to an acoustic telephone ring. Again, the sensory mechanisms are the same for all incoming messages.

The fact that the user can specify which particular alerting mechanism(s) are employed is advantageous, but the techniques for doing so in the prior art are somewhat limited. Therefore, the need exists for a more flexible technique that a user can use to specify the alerting mechanism on his or her telecommunications terminal.

SUMMARY OF THE INVENTION

The present invention enables a user to specify the alerting mechanism(s) of a telecommunications terminal without some of the costs and disadvantages for doing so in the prior art. In particular, the illustrative embodiment enables a telecommunications terminal to determine which mechanism(s) to use to alert the user to the arrival of an incoming message based on one or more of the following: some property of the incoming message (e.g., who sent the message, a priority level associated with the message, the semantic content of the message, the length of the message, etc.), the time and date (i.e., the "calendrical time"), environmental parameters (e.g., temperature, ambient luminosity, etc.), the user's physiological parameters (e.g., blood pressure, heart rate, gender, etc.), properties of the caller (e.g., the caller's gender, age, physiological parameters, etc.), the location of the user, the proximity of other telecommunications terminals in the vicinity, and whether the user is currently receiving another message. For example, it might be appropriate to alert a user via a vibration mechanism rather than an acoustic mechanism in a noisy environment, or when there are many telecommunications terminals nearby The illustrative embodiment also enables a telecommunications terminal to determine which properties and/or components of the incoming message should be communicated to the user via the alerting mechanism, also based on the information enumerated above. For example, the visual alerting mechanism of a telecommunications terminal might display the "From" and "Subject" fields of an email message from a known party, but simply display a generic symbol for the arrival of an email message from an unknown party. The illustrative embodiment enables a user to program his or her telecommunications terminal to provide the desired behavior.

The illustrative embodiment comprises: a receiver for receiving an incoming signal directed to a telecommunications terminal, wherein said incoming signal is characterized by at least one property; a plurality of transducers, wherein each of said transducers can alert a user to the arrival of said incoming signal; and a processor for selecting which of said transducers alert said user based on at least one property of said incoming signal.

DETAILED DESCRIPTION

Figure 1:
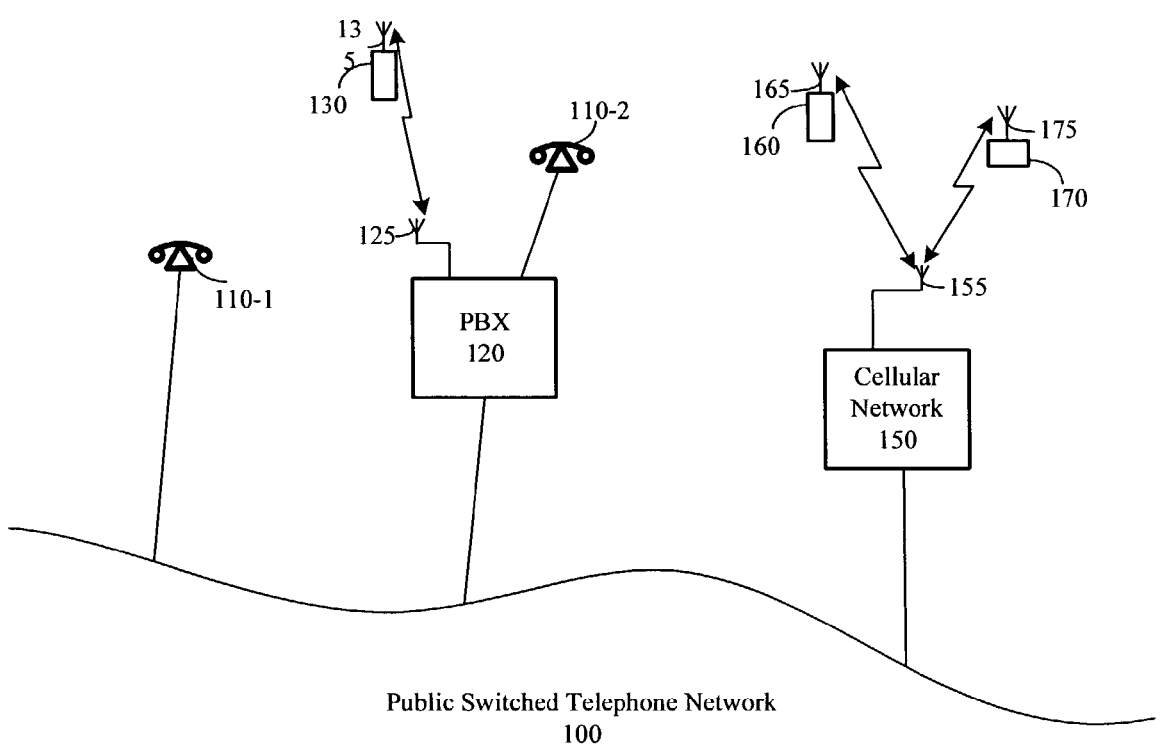
FIG. 1 depicts a block diagram of an exemplary subnetwork attached to public switched telephone network (PSTN) 100.
Figure 2:
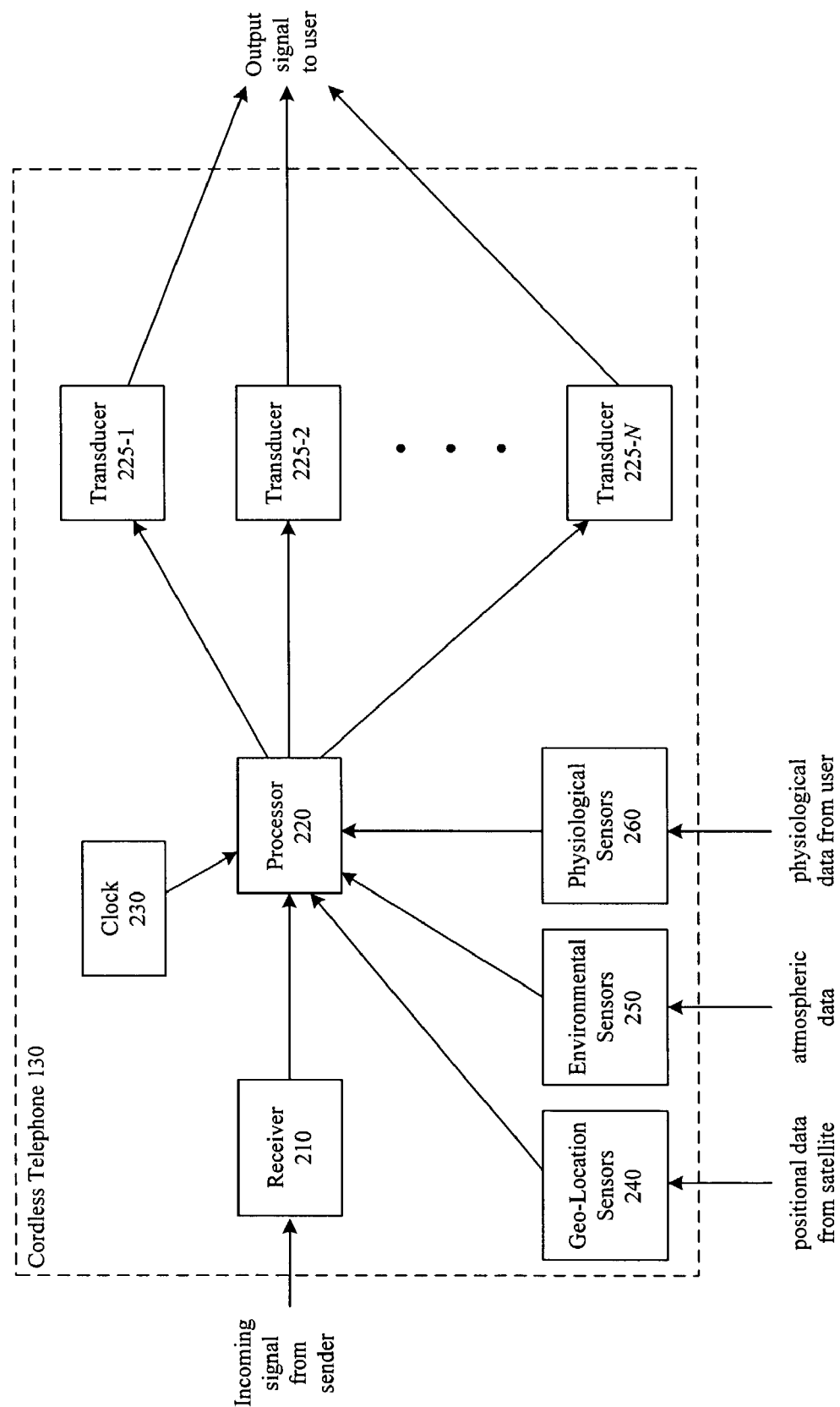
FIG. 2 depicts a block diagram of cordless telephone 130, as shown in FIG. 1, in accordance with the illustrative embodiment of the present invention.

FIG. 2 depicts a block diagram of the salient components of cordless telephone 130, in accordance with the illustrative embodiment of the present invention. Cordless telephone 130 comprises: receiver 210, processor 220, clock 230, geo-location sensors 240, environmental sensors 250, physiological sensors 260, and transducers 225-1 through 225-N, interconnected as shown.

Clock 230 transmits the current time, date, and day of the week to processor 220 in well-known fashion.

Geo-location sensors 240 receive positional data, as is described in detail below, and transmit these data to processor 220 in well-known fashion.

Environmental sensors 250 receive atmospheric data, as is described in detail below, and transmit these data to processor 220 in well-known fashion.

Physiological sensors 260 receive atmospheric data, as is described in detail below, and transmit these data to processor 220 in well-known fashion.

Processor 220 receives an incoming message (e.g., a telephone call, a fax, an e-mail, etc.) from a remote user, in well-known fashion, and determines, based on the inputs it receives, as described above, and properties of the incoming message, (1) which transducers should alert the user to the arrival of the incoming message, and (2) what information content from the incoming message should be communicated to the user in the alert. Details concerning how processor 220 makes such determinations are given below.

The appropriate transducers 225, as determined above by processor 220, generate an output signal based on the appropriate information content, again as determined above by processor 220, in well-known fashion. For example, an acoustic transducer could generate a musical jingle or a human-like voice based on the sender and/or priority of the message, while a visual transducer could display the text in the subject line of an email message or a graphical symbol based on some property of the email message.

Figure 3:
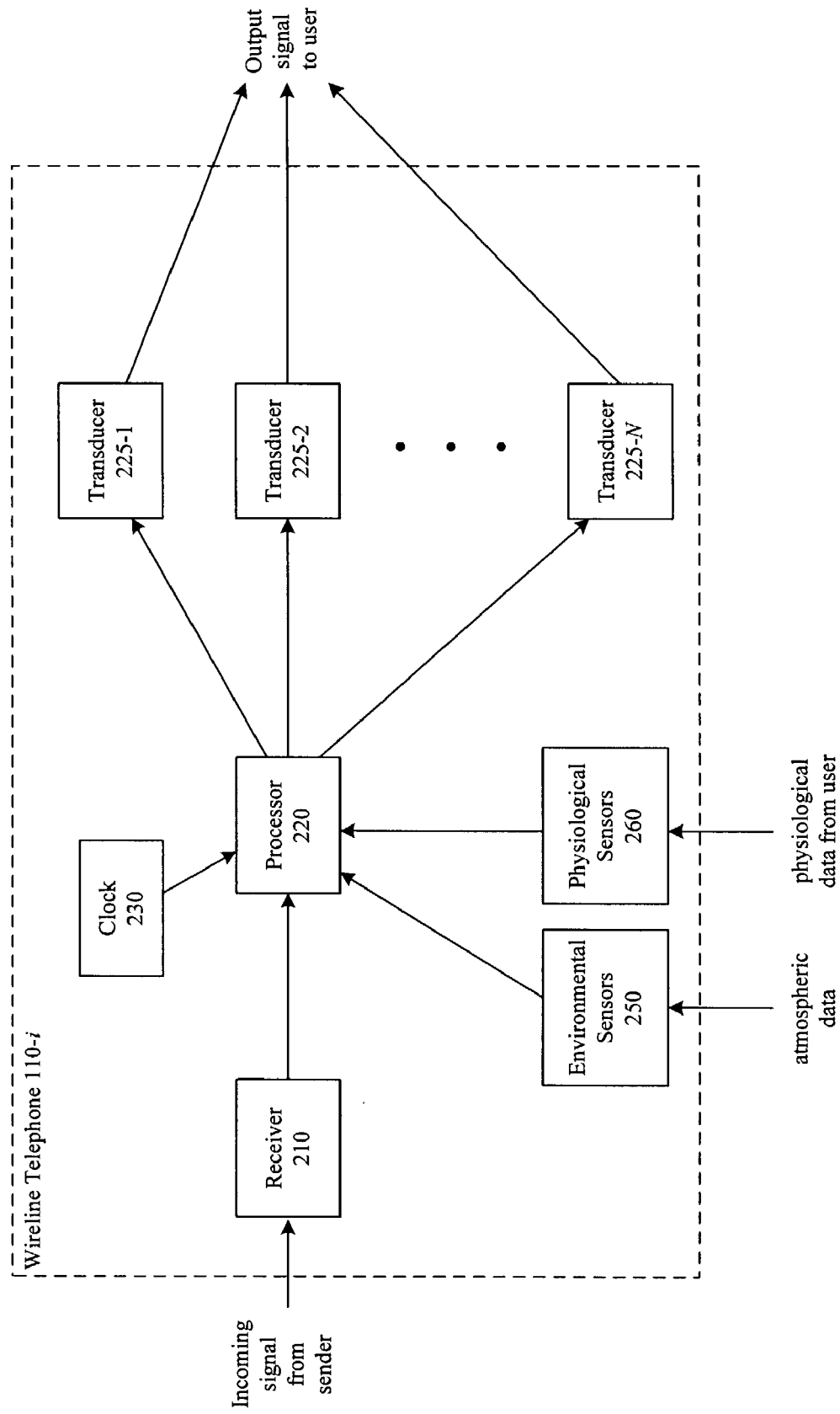
FIG. 3 depicts a block diagram of wireline telephone 110-*i*, as shown in FIG. 1, in accordance with the illustrative embodiment of the present invention.

FIG. 3 depicts a block diagram of the salient components of wireline telephone 110-*i*, in accordance with the illustrative embodiment of the present invention. Wireline telephone 110-*i* comprises: receiver 210, processor 220, clock 230, environmental sensors 250, physiological sensors 260, and transducers 225-1 through 225-N, interconnected as shown. As can be seen by comparing FIG. 3 with FIG. 2, wireline telephone 110-*i* is similar to cordless telephone 130, with the exception that wireline telephone 110-*i* does not have geo-location sensors 240, which are superfluous in a wireline terminal at a fixed position.

Figure 4:
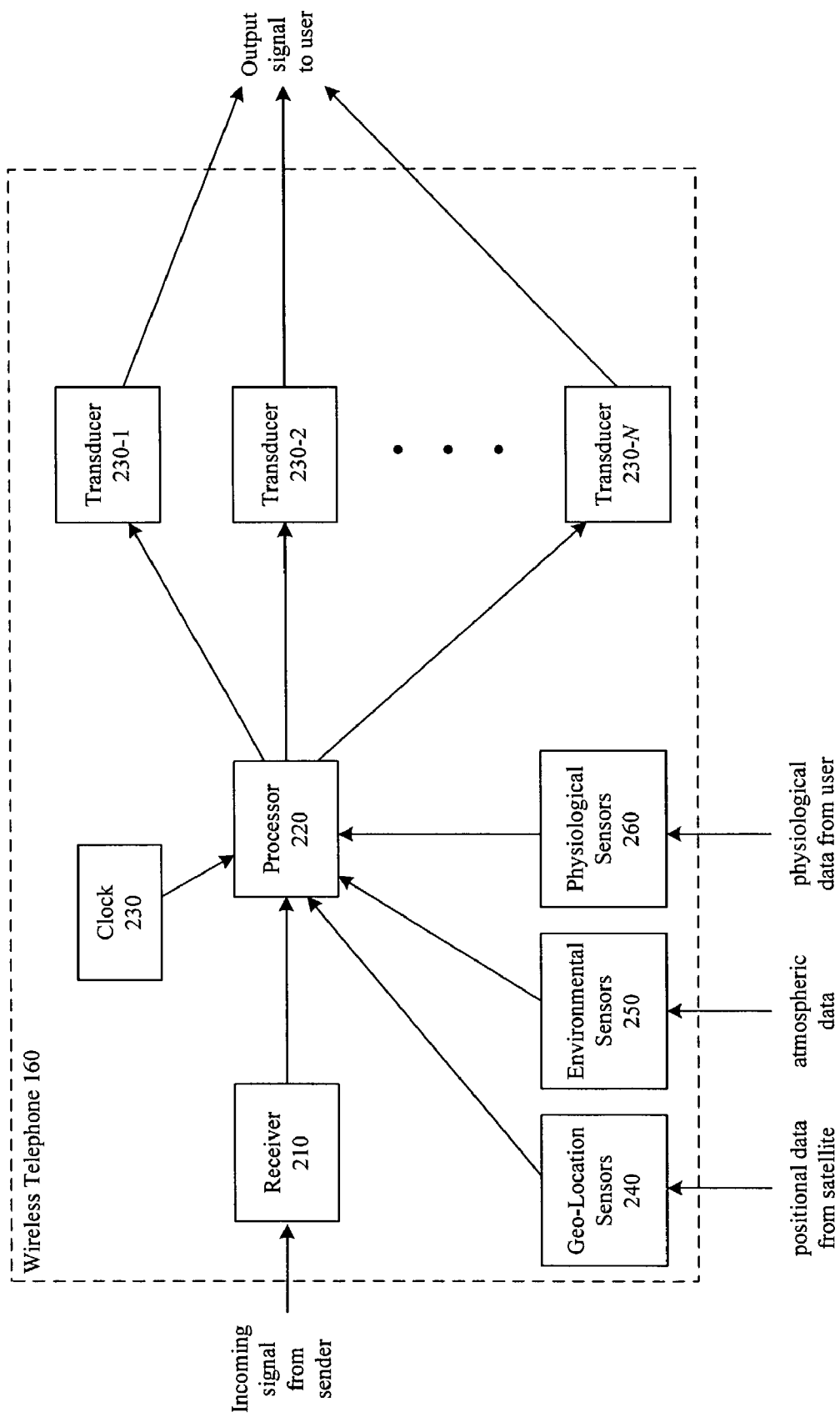
FIG. 4 depicts a block diagram of wireless telephone 160, as shown in FIG. 1, in accordance with the illustrative embodiment of the present invention.

FIG. 4 depicts a block diagram of the salient components of wireless telephone 160, in accordance with the illustrative embodiment of the present invention. Wireline telephone 110-*i* comprises: receiver 210, processor 220, clock 230, geo-location sensors 240, environmental sensors 250, physiological sensors 260, and transducers 225-1 through 225-N, interconnected as shown. As can be seen by comparing FIG. 4 with FIG. 2, wireless terminal 160 is similar to wireless terminal 130. It will also be clear to those of ordinary skill in the art how to apply the architecture of FIG. 4 to other wireless terminals such as two-way pagers, personal digital assistants (PDAs), etc.

Figure 5:
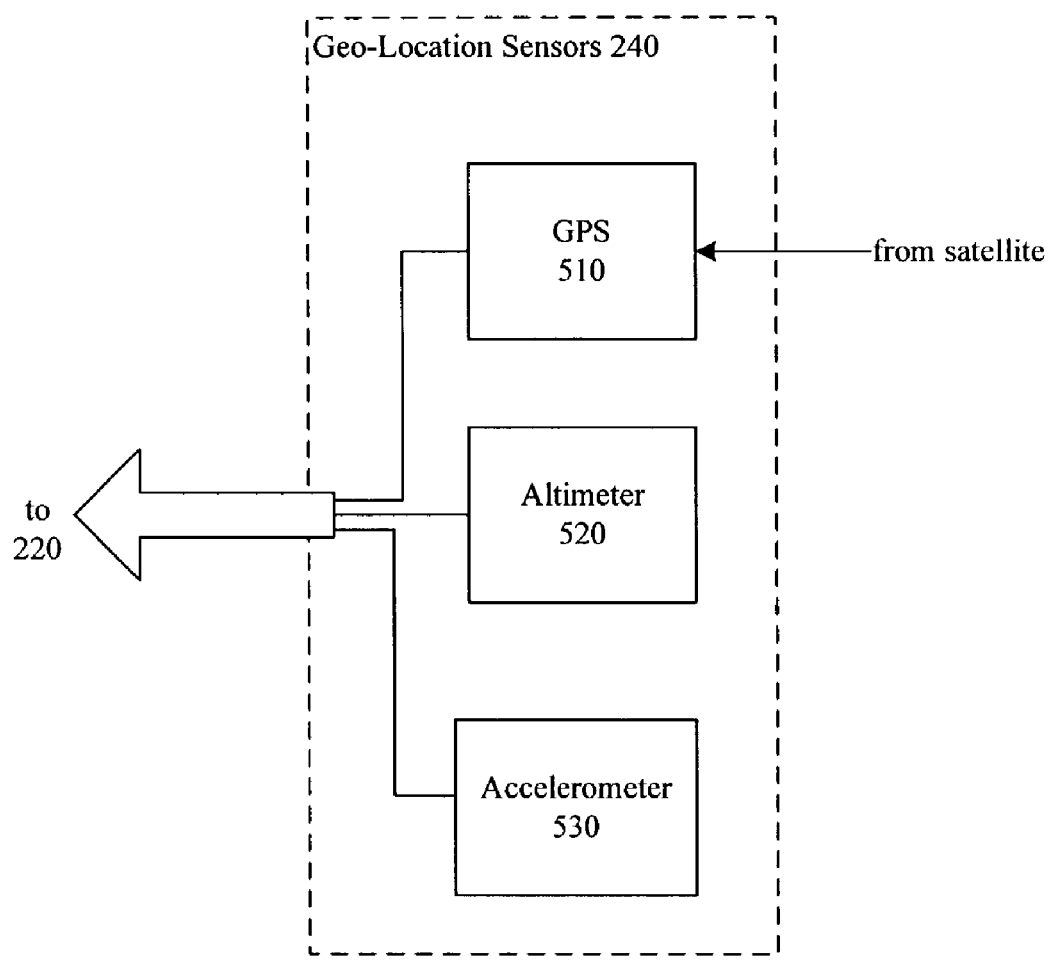
FIG. 5 depicts a block diagram of geo-location sensors 240, as shown in FIG. 2 and FIG. 4, in accordance with the illustrative embodiment of the present invention.

FIG. 5 depicts a block diagram of the salient components of geo-location sensors 240, in accordance with the illustrative embodiment of the present invention. Geo-location sensors 240 comprises: global positioning system (GPS) 510, altimeter 520, and accelerometer 530.

GPS 510 receives satellite-based signals and determines global position, as is well understood in the art, and transmits the data to processor 220. In some embodiments, GPS 510 also transmits information to processor 220 concerning the geo-locations of other wireless terminals in the vicinity; as described below, processor 220 can consider this information in determining how to alert the user to the arrival of the incoming message.

It will be clear to persons skilled in the art that some embodiments might employ means other than satellite-based signals for determining geo-location (e.g., triangulation, radio beacons, radio-frequency fingerprinting [U.S. Pat. No. 6,393,294, incorporated by reference], etc.) In such embodiments, an appropriate receiver (e.g., radio-frequency receiver, etc.) would be substituted for GPS 510, as is well understood in the art.

Altimeter 520 measures altitude, in well-known fashion, and transmits its measurements to processor 220; in some embodiments altimeter 520's readings are based on barometric pressure, and in some other embodiments altimeter 520 is radar-based.

Accelerometer 530 measures acceleration, in well-known fashion, and transmits its measurements to processor 220.

Figure 6:
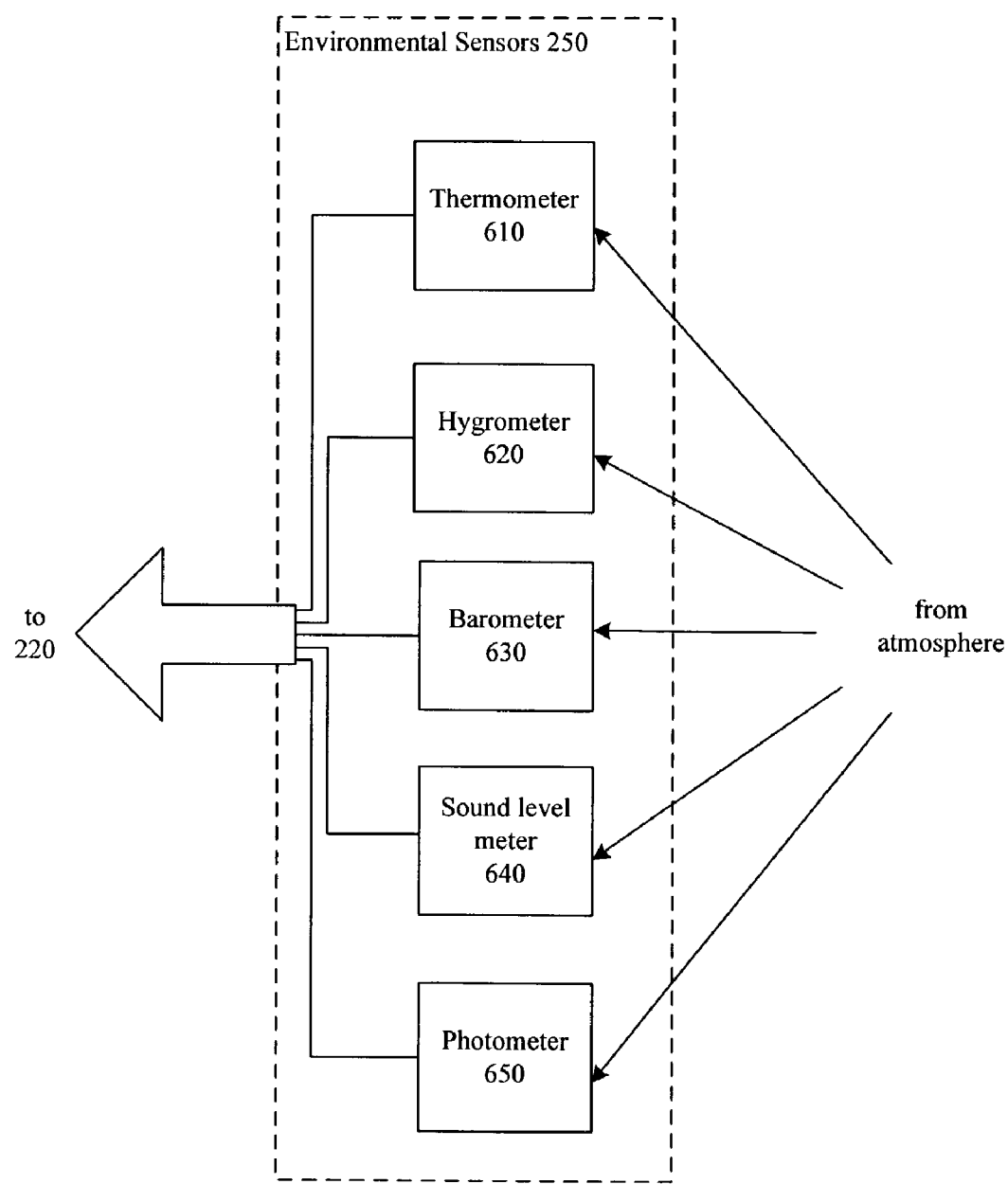
FIG. 6 depicts a block diagram of environmental sensors 250, as shown in FIGS. 2, 3, and 4, in accordance with the illustrative embodiment of the present invention.

FIG. 6 depicts a block diagram of the salient components of environmental sensors 250, in accordance with the illustrative embodiment of the present invention. Environmental sensors 250 comprises: thermometer 610, hygrometer 620, barometer 630, sound level meter 640, and photometer 650, all of which receive information from the atmosphere.

Thermometer 610 measures ambient temperature, in well-known fashion, and transmits its measurements to processor 220.

Hygrometer 620 measures ambient humidity, in well-known fashion, and transmits its measurements to processor 220.

Barometer 630 measures ambient air pressure, in well-known fashion, and transmits its measurements to processor 220.

Sound level meter 640 measures ambient sound intensity, in well-known fashion, and transmits its measurements to processor 220.

Photometer 650 measures ambient light intensity, in well-known fashion, and transmits its measurements to processor 220.

Figure 7:
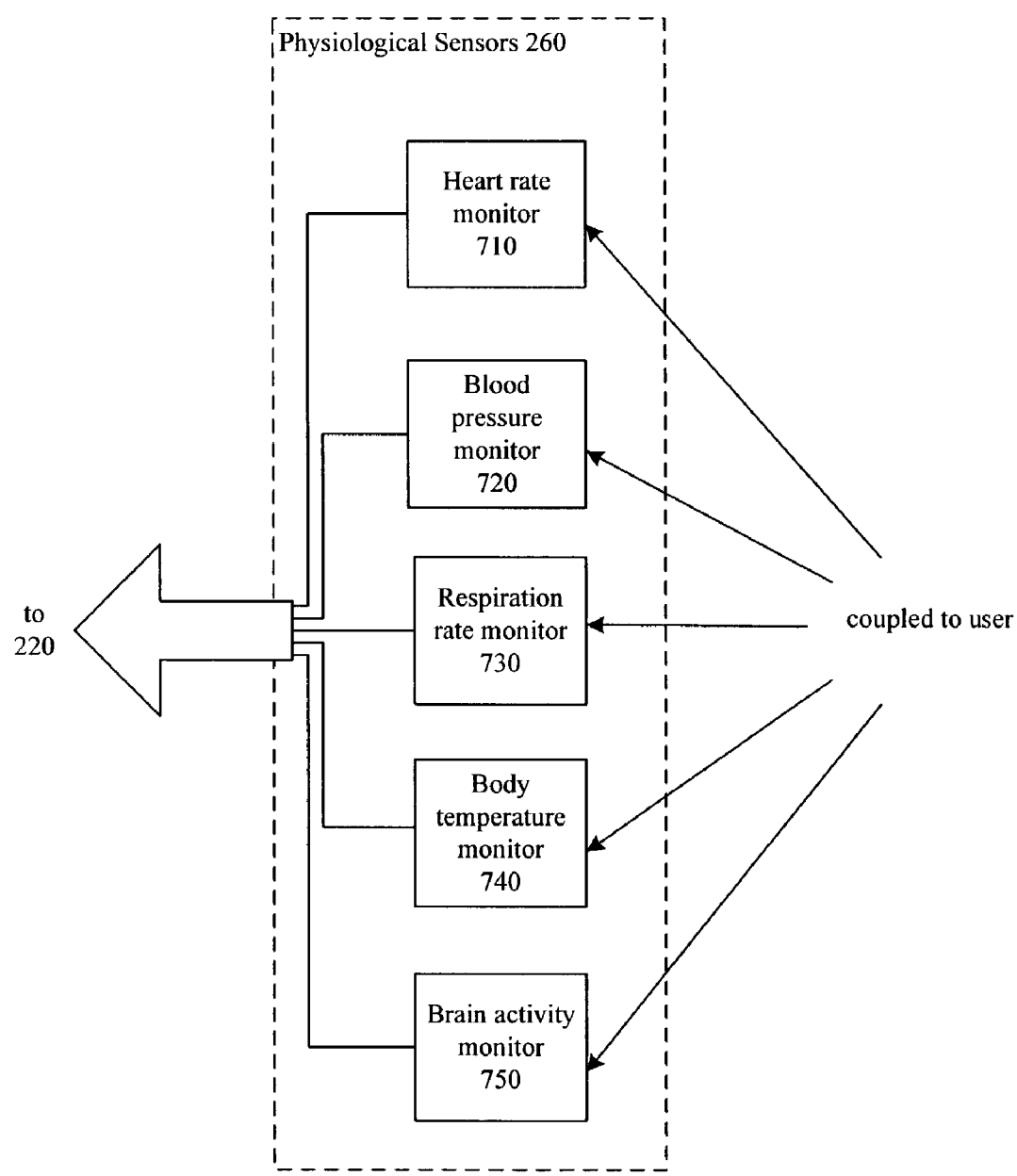
FIG. 7 depicts a block diagram of physiological sensors 260, as shown in FIGS. 2, 3, and 4, in accordance with the illustrative embodiment of the present invention.

FIG. 7 depicts a block diagram of the salient components of physiological sensors 260, in accordance with the illustrative embodiment of the present invention. Physiological sensors 260 comprises: heart rate monitor 710, blood pressure monitor 720, respiration rate monitor 730, body temperature monitor 740, and brain activity monitor 750. In some embodiments, at least one of these monitors receives input from the user via at least one sensor coupled to a part of a user's body (e.g., finger, forehead, etc.), wherein the sensor transmits data to the terminal either by a wire, or wirelessly. In some other embodiments, at least one of these monitors receives input from the user via at least one sensor located within the terminal, wherein the sensor receives physiological signals from the user when the user is holding the terminal.

Heart rate monitor 710 measures the user's heart rate, in well-known fashion, and transmits its measurements to processor 220.

Blood pressure monitor 720 measures the user's blood pressure, in well-known fashion, and transmits its measurements to processor 220.

Respiration rate monitor 730 measures the user's respiration rate, in well-known fashion, and transmits its measurements to processor 220.

Body temperature monitor 740 measures the user's body temperature, in well-known fashion, and transmits its measurements to processor 220.

Brain activity monitor 750 measures the user's brain activity in well-known fashion (e.g., EKG, etc.), and transmits its measurements to processor 220.

Figure 8:
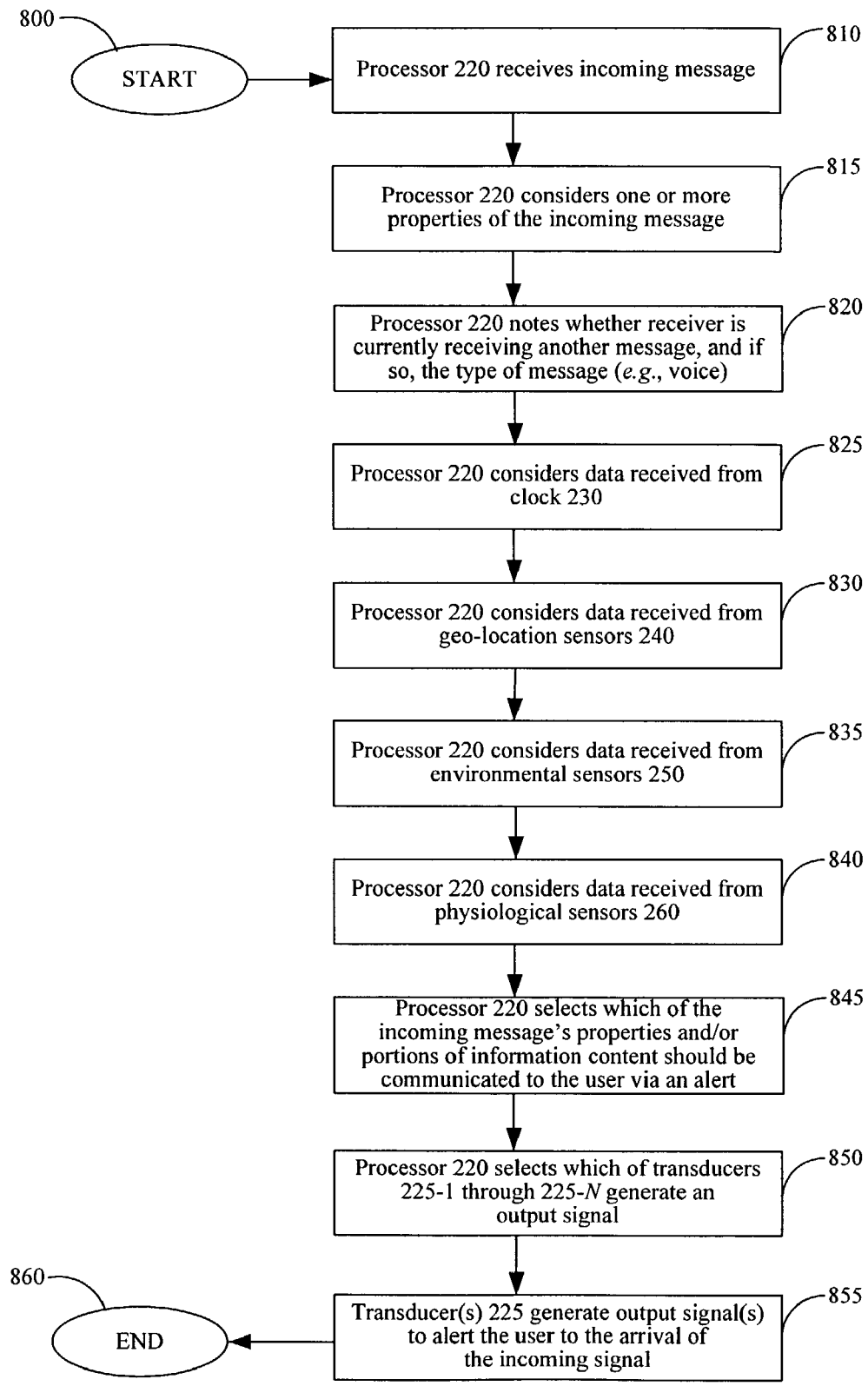
FIG. 8 depicts a flowchart of the operation of processor 220, as shown in FIGS. 2, 3, and 4, in accordance with the illustrative embodiment of the present invention.

FIG. 8 depicts a flowchart of the operation of processor 220 according to the present invention.

At task 810, processor 220 receives an incoming message from a remote user.

At task 815, processor 220 considers one or more properties of the incoming message for determining how to alert the user to the arrival of the incoming message. In some embodiments such properties can include: the sender of the message, properties of the sender (e.g., the caller's gender, age, etc.), a priority associated with the message, the semantic content of the subject and/or body of the message, the length of the message, etc.

At task 820, processor 220 notes whether receiver 210 is currently receiving another message, and if so, what type of message (e.g., voice, email, etc.), for determining how to alert the user to the arrival of the incoming message.

At task 825, processor 220 considers data received from clock 230 for determining how to alert the user to the arrival of the incoming message.

At task 830, processor 220 considers data received from geo-location sensors 240 for determining how to alert the user to the arrival of the incoming message. As indicated above, these data can indicate the most appropriate manner in which a user should be alerted to an incoming message; for example, it might be advantageous to alert a user inside a church or movie theater via a vibration transducer (the theory being that there are some places where an acoustic alert would disturb others.)

At task 835, processor 220 considers data received from environmental sensors 250 for determining how to alert the user to the arrival of the incoming message; for example, it might be advantageous to alert a user via a vibration transducer in a noisy environment (the theory being that the user might not hear the alert.)

At task 840, processor 220 considers data received from physiological sensors 260 for determining how to alert the user to the arrival of the incoming message; for example, it might be advantageous to alert a user via an acoustic transducer when a user is sleeping (the theory being that either (a) the user might not have the phone on his/her person, or (b) if the user does have the phone on his/her person, the vibration may not be sufficient to awaken the user.)

At task 845, processor 220 decides, based on (i) how its user has programmed it; (ii) properties of the incoming message; (iii) whether receiver 210 is currently receiving another message, and if so, what type of message; and (iv) the data from clock 230, geo-location sensors 240, environmental sensors 250, and physiological sensors 260; which of the incoming message's properties and/or portions of information content should be communicated via an alert (e.g., the "subject" field of an email message, the length of the message, the priority of the message, etc.)

At task 850, processor 220 decides, again based on (i) how its user has programmed it; (ii) properties of the incoming message; (iii) whether receiver 210 is currently receiving another message, and if so, what type of message; and (iv) the data from clock 230, geo-location sensors 240, environmental sensors 250, and physiological sensors 260; which transducer(s) 225-1 through 225-N should alert the user to the arrival of the incoming message.

At task 855, transducer(s) 255 selected in task 850 generate output signal(s) containing the information selected in task 845. It will be clear to those skilled in the art how to generate such output signals; for example, an acoustic transducer could generate a musical signal or a human-like voice to alert the user, while a visual transducer could generate text or graphic symbols to alert the user, as is well understood in the art.

It is to be understood that the above-described embodiments are merely illustrative of the present invention and that many variations of the above-described embodiments can be devised by those skilled in the art without departing from the scope of the invention. It is therefore intended that such variations be included within the scope of the following claims and their equivalents.

What is claimed is:

1. A method comprising:
   receiving a signal at a first telecommunications terminal; and
   determining which of a plurality of transducers of said first telecommunications terminal to use to notify the user of said first telecommunications terminal of the arrival of said signal;
   wherein the determination of which of said plurality of transducers to use is based on the proximity of said first telecommunications terminal to a second telecommunications terminal.

2. The method of claim 1 wherein the determination is also based on the identity of the sender of said signal.

3. The method of claim 1 wherein the determination is also based on the geo-location of said telecommunications terminal.

4. The method of claim 1 wherein the determination is also based on the value of an environmental parameter at said telecommunications terminal.

5. The method of claim 1 wherein the determination is also based on the semantic content of said signal.

6. The method of claim 5 wherein the determination is also based on the relevance of said semantic content to the user of said second telecommunications terminal.

7. A method comprising:
   receiving a signal at a telecommunications terminal; and
   determining which of a plurality of transducers of said telecommunications terminal to use to notify the user of said telecommunications terminal of the arrival of said signal;
   wherein the determination of which of said plurality of transducers is based on a physiological parameter of said user.

8. The method of claim 7 wherein the determination is also based on the identity of the sender of said signal.

9. The method of claim 7 wherein the determination is also based on the calendrical time at said telecommunications terminal.

10. The method of claim 7 wherein the determination is also based on the geo-location of said telecommunications terminal.

11. The method of claim 7 wherein the determination is also based on the value of an environmental parameter at said telecommunications terminal.

12. A method comprising:
    receiving a signal at a telecommunications terminal; and
    determining which of a plurality of transducers of said telecommunications terminal to use to notify the user of said telecommunications terminal of the arrival of said signal;
    wherein the determination of which of said plurality of transducers is based on the semantic content of said signal and the calendrical time at said telecommunications terminal.

13. The method of claim 12 wherein the determination is also based on the identity of the sender of said signal.

14. The method of claim 12 wherein the determination is also based on whether said telecommunications terminal is receiving another incoming signal.

15. The method of claim 12 wherein the determination is also based on the geo-location of said telecommunications terminal.

16. The method of claim 12 wherein the determination is also based on the value of an environmental parameter at said telecommunications terminal.

17. A method comprising:
  receiving a signal at a telecommunications terminal; and
  determining which of a plurality of transducers of said telecommunications terminal to use to notify the user of said telecommunications terminal of the arrival of said signal;
  wherein the determination of which of said plurality of transducers is based on the semantic content of said signal and whether or not said telecommunications terminal is receiving another incoming signal.

18. The method of claim 17 wherein the determination is also based on the identity of the sender of said signal.

19. The method of claim 17 wherein the determination is also based on the geo-location of said telecommunications terminal.

20. The method of claim 17 wherein the determination is also based on the value of an environmental parameter at said telecommunications terminal.

* * * * *